United States Patent [19]

Dowrick

[11] Patent Number: 4,876,086
[45] Date of Patent: Oct. 24, 1989

[54] INJECTABLE COMPOSITIONS OF AMOXYCILLIN TRIHYDRATE

[75] Inventor: John S. Dowrick, Littlehampton, England

[73] Assignee: Beecham Group p.l.c., England

[21] Appl. No.: 98,326

[22] Filed: Sep. 17, 1987

Related U.S. Application Data

[63] Continuation of Ser. No. 822,842, Jan. 27, 1986, abandoned, which is a continuation of Ser. No. 679,916, Dec. 10, 1984, abandoned, which is a continuation of Ser. No. 432,924, Oct. 5, 1982, abandoned, which is a continuation of Ser. No. 156,363, Jun. 4, 1980, abandoned, which is a continuation of Ser. No. 949,241, Oct. 6, 1978, abandoned, which is a continuation of Ser. No. 748,696, Dec. 8, 1976, abandoned, and a continuation-in-part of Ser. No. 661,370, Feb. 25, 1976, abandoned, and a continuation-in-part of Ser. No. 661,372, Feb. 25, 1976, abandoned.

[30] Foreign Application Priority Data

Mar. 7, 1975 [GB] United Kingdom ............. 09515

[51] Int. Cl.$^4$ ............... H61K 31/79; H61K 31/43
[52] U.S. Cl. ................................. 424/80; 514/197
[58] Field of Search ............... 424/80, 114; 514/197

[56] References Cited

U.S. PATENT DOCUMENTS

| 2,897,120 | 7/1959 | Cronin et al. | 514/199 |
| 2,939,818 | 6/1960 | Berger | 514/199 |
| 3,062,718 | 11/1969 | Spiegel | 424/115 |
| 3,674,776 | 7/1972 | Long et al. | 260/239.1 |
| 3,969,524 | 7/1976 | Emodi et al. | 514/197 |
| 4,423,033 | 12/1983 | Taskis | 424/80 |

FOREIGN PATENT DOCUMENTS 1289693 9/1972 United Kingdom .

OTHER PUBLICATIONS

*The Theory & Practice of Industrial Pharmacy*, pp. 108–110 (1976).

Primary Examiner—Jerome D. Goldberg
Attorney, Agent, or Firm—Jacobs & Jacobs

[57] ABSTRACT

Injectable pharmaceutical compositions are provided which comprise fine particles of amoxycillin trihydrate coated with a dispersing agent, the ratio of amoxycillin trihydrate to dispersing agent being from 1000:1 to 20:1. A preferred dispersing agent is a mixture of polyvinylpyrrolidone and lecithin. Such compositions give surprising prolonged blood levels of amoxycillin after administration. The compositions can be used in the treatment of both humans and domestic animals.

7 Claims, No Drawings

INJECTABLE COMPOSITIONS OF AMOXYCILLIN TRIHYDRATE

The present invention relates to injectable compositions containing amoxycillin trihydrate.

Amoxycillin is a broad spectrum antibacterial agent the preparation and many properties of which are described in British Patent Specification No. 1,241,844.

It is frequently desirable to administer antibacterial agents by injection. A particularly suitable method of injecting penicillins is to use a solution of a sodium salt of the penicillin. It is possible to do this with such conventional penicillins as ampicillin, benzylpenicillin, cloxacillin, amoxycillin, and the like; however, such known injectable compositions containing an aqueous solution of sodium amoxycillin tend to have a somewhat shorter serum half life than is desirable after administration.

An injectable composition of amoxycillin has now been discovered that has the advantage of producing unusually sustained effective levels of the anti-biotic in the blood of humans and domestic animals after conventional administration. Further, this composition after make up for injection has good stability, good needling properties and it is well tolerated on administration.

Accordingly the present invention provides a pharmaceutical composition in the form of a powder which may be constituted to an injectable composition by the addition of an aqueous vehicle which composition comprises fine particles of amoxycillin trihydrate coated by a dispersing agent, the ratio of amoxycillin trihydrate to dispersing agent being from 1000:1 to 20:1.

When used herein the term 'pharmaceutical composition' includes veterinary composition.

Naturally, the composition of this invention will be pharmaceutically acceptable, sterile and pyrogen free.

All ratios used herein are calculated on a weight/weight basis.

When used herein the term 'fine particles' means particles of an average diameter of from $2\mu$ to $20\mu$ at least 95% of which have diameters of between $0.5\mu$ and $50\mu$. More suitably these fine particles have an average diameter of from $4\mu$ to $10\mu$ and at least 95% of which have diameters of between $1\mu$ and $30\mu$.

When used herein the term 'aqueous vehicle' means a pharmaceutically acceptable liquid which consists of water or which consists essentially of water to which has been added small amounts of conventional materials such as (a) ionic salts to adjust the tonicity of the final suspension, (b) buffers, (c) preservatives or (d) other conventional materials used in injectable compositions. Particularly suitable vehicles for addition to compositions of this invention are water and saline solutions. A preferred vehicle for addition to the compositions of this invention is water for injection.

When used herein the term 'coated' means that 10% to 100% of the surface of the fine particle is covered by the dispersing agent. It is believed that it is advantageous to cover as much as possible of the surface of the fine particles., for example 80–100% of the surface, preferably substantially 100% of the surface.

When used herein the term 'dispersing agent' means a mixture of substances which comprises at least one water soluble polymeric material of average molecular weight 6,000 to 400,000, and a wetting agent. Normally the polymeric material will represent the major part of the dispersing agent, and the wetting agent the minor part.

Suitable polymeric materials for use in this invention will include polymers known to be suitable for injection such as polyvinylpyrrolidone, vinyl pyrrolidone/vinyl acetate copolymers, sodium carboxymethyl cellulose, polyvinylalcohol, dextran and sodium alginate. Of these polymeric materials polyvinylpyrrolidone, sodium carboxymethylcellulose, vinyl pyrrolidone/vinyl acetate copolymers and dextran are usually found to be the most suitable, and we believe that polyvinylpyrrolidone is a preferred polymer for use in this invention.

Generally the molecular weight of the polymer used in the dispersing agent is from 10,000 to 60,000, for example, 10,000 to 40,000.

Suitable wetting agents include those known to be suitable for injection such as lecithin; phospholipids; sorbitan fatty esters such as mono-fatty esters, for example the mono-palmitate and mono-oleate, and tri-fatty esters, for example the tri-oleate, and in general those fatty esters sold under the Trade Mark 'SPAN'; polyoxyalkylene sorbitan fatty esters such as the mono-palmitate, mono- or tri-oleate, and in general those fatty esters sold under the Trade Mark 'TWEEN'; and polyoxyalkylene castor oil, such as polyoxyethylated castor oil; and in general ethyleneoxide/sugar ester condensates; and the like. Of these wetting agents lecithin and polyoxyalkylene castor oil, such as polyoxyethylated castor oil, will often be preferred. Lecithin is a particularly suitable wetting agent for use in this invention.

Generally the ratio of polymer to wetting agent present in the dispersing agent will be from 12:1 to 1:12, suitable 12:1 to 1:3, more suitably from 10:1 to 1:2 and preferably from about 8:1 to about 1:1, for example, about 5:1.

A particularly suitable ratio of amoxycillin trihydrate to wetting agent is from 400:1 to 100:1.

Normally the ratio of amoxycillin trihydrate to dispersing agent will be 200:1 to 20:1.

A particularly suitable ratio of amoxycillin trihydrate to dispersing agent is believed to be from 100:1 to 25:1.

Thus a preferred composition of this invention will comprise fine particles of amoxycillin trihydrate coated by a mixture of lecithin and polyvinylpyrrolidone wherein the ratio of amoxycillin trihydrate to the mixture of lecithin and polyvinylpyrrolidone is from 100:1 to 25:1 and the ratio of lecithin to polyvinylpyrrolidone is from 1:10 to 2:1. Preferably the latter ratio will be in the range 1:10 to 1:2.

If desired the compositions of this invention may also contain other antibiotics in a form suitable for injection. Suitable additional antibiotics for inclusion include ampicillin trihydrate, sodium ampicillin, methicillin, cloxacillin, flucloxacillin, naphthcillin and the like either in the form of a sparingly soluble salt or in the form of fine particles coated with a suspending agent. When present, the ratio of the additional antibiotic to amoxycillin trihydrate is normally from 5:1 to 1:5 and more usually from 2:1 to 1:2, for example approximately 1:1. Ampicillin trihydrate is believed to be particularly suitable for such use.

The composition of this invention may also contain conventional pharmaceutically acceptable additives used in the preparation of injectable compositions; such conventional additives include buffers, preservatives and salts required to render the final injectable suspension of suitable tonicity. These additives may merely be mixed into the formulated compositions, or may themselves be coated with dispersing agent at the same time as, or separately from, the amoxycillin trihydrate. In some cases compatible additives can be incorporated into the coating layer of dispersing agent. Additives such as buffers and salts required to render the final injectable suspension of suitable tonicity may if desired be incorporated into the aqueous vehicle used for constitution of the composition.

Normally the buffers which may be used will be chosen so that the pH of the injectable suspension will enhance the stability of the suspension, for example the pH of the suspension will normally be from 5 to 8.5 and more usually 5.5 to 6.5. Suitable buffers for this purpose include sodium salts of organic acids, for example trisodium citrate, sodium acetate and the like or physiochemically similar salts such as the sodium salts of phosphoric acid, for example, disodium phosphate. Frequently the compositions of this invention will contain from 2–6% of such salts based on the total weight of the composition.

Any compatible conventional preservatives may be used in the composition of the invention. It is presently believed that conventional esters of hydroxybenzoic acid are suitable agents and that these may be included by from 0.05% to 1% of the weight of amoxycillin trihydrate present.

If the compositions of the invention are to be made up into the injectable suspension by the addition of normal saline or the like then it is not usual to include additional ionic salts in the powder. However, if the compositions of the invention are to be made up by the addition of sterile water then it is advantageous to include at least one ionic salt and this will usually be a sodium salt of a strong acid. It has been found that sodium chloride is particularly useful for this purpose.

It is presently believed that particularly suitable compositions of this invention will include up to 2% of sodium chloride expressed relative to the weight of amoxycillin trihydrate present and that certain preferred compositions will contain 0.5–1% of sodium chloride.

The invention also describes a process for the preparation of the pharmaceutical compositions of the invention, which process comprises coating fine particles of amoxycillin trihydrate with a dispersing agent.

This process will often be carried out by mixing the amoxycillin trihydrate with a solution of the dispersing agent in an inert organic solvent, and then drying the mixture. Suitable organic solvents for this use should be relatively volatile to facilitate the drying step, and include chlorinated hydrocarbons such as chloroform and methylene dichloride, alcohols such as isopropanol, and the like.

The required fine particles can be prepared by conventional milling procedures.

Other processes for coating the fine particles of amoxycillin trihydrate include any convenient method known to the skilled formation chemist for producing coated particles such as spray-coating, coascervation, freezedrying, co-granulation and the like. Standard text books such as "The Theory and Practice of Industrial Pharmacy" by L. Lachman et al., Lea and Feliger, Philadelphia (1970), described processes which may be readily adapted to the production of the compositions of this invention now that the surprising discovery has been made that such compositions possess desirable properties such as the ability to provide prolonged blood levels.

To be suitable for injection the compositions must be sterile. This can be achieved by using sterile ingredients and conditions in the preparation of the compositions, or by sterilising the compositions after their formulation in the usual manner.

The composition of this invention may be presented in the usual way in unit or multi-dose form in vials or ampoules or the like.

For use in human therapy such forms will normally contain between 100 and 1200 mg. of amoxycillin trihydrate (measured as amoxycillin), suitably between 200 and 600 mg. of amoxycillin trihydrate, for example 250 and 500 mg. of amoxycillin trihydrate.

These compositions will be made up with the aqueous vehicle in conventional manner, and the concentration of the resultant suspension chosen so as to give a convenient injection volume. For example the injection volume will normally be in the range 0.5 to 1.5 ml. The concentration of the injected suspension will often be between 30 and 500 mg/ml., suitably 30–3000 mg/ml.. Within this latter range concentrations such as 50, 100, 200 and 250 mg/ml. will often be particularly suitable due to ease of calculation of the required volumes. It has been found that for a given dosage a higher concentration of injected suspension will often provide more prolonged effective blood levels of antibiotic than a lower concentration of injected suspension.

The actual weight of amoxycillin trihydrate administered in single dose will depend in the usual way on various factors such as for example the nature of the bacterial infection and the severity of the infection. However we have found that a dose of between 3 and 10 mg/kg body weight of amoxycillin trihydrate (measured as amoxycillin) is generally suitable.

In a further aspect this invention provides a method of treating bacterial infections in humans which method comprises the injection of a suspension of amoxycillin trihydrate which suspension was formed by the addition of an aqueous vehicle to a composition of this invention.

Once made up such suspensions have good stability.

An alternative view of this aspect of the invention provides a method of obtaining prolonged useful blood levels of amoxycillin in humans which method comprises the parenteral administration of a suspension of amoxycillin trihydrate which suspension was formed by the addition of an aqueous vehicle to a composition of this invention.

The administration is normally intra-muscular or subcutaneous. Parenteral administration includes injection and infusion.

In human therapy it will be realised that the prolonged blood levels obtainable with the composition of the invention will be of great advantage, particularly in maintaining an effective blood level of amoxycillin during the night hours when further administration is normally inconvenient.

Similarly for the treatment of out-patients it is often difficult to arrange frequently repeated injections.

From the aforesaid it will be clear that a particularly suitable method of the invention will comprise the administration of one or two injections per day only, and a preferred method of the invention will often comprise the administration of not more than one injection per day.

It is further believed that when rather larger quantities of the composition are injected, blood levels effective against certain susceptible bacteria may be maintained for more than one day. Thus the invention further provides a method of treating highly susceptible bacterial infections in humans which method comprises the injection not more than once every two days of an effective amount of amoxycillin trihydrate in the form of a composition of the invention suspended in an aqueous vehicle.

Normally the effective amount of amoxycillin trihydrate will be in the range 10 to 30 mg/kg measured as amoxycillin. Suitably this dosage is 15 to 25 mg/kg, for example about 20mg/kg. These higher levels of antibiotic are most suitably administered by divided injections at more than one site, for example by two injections of half the required amount.

It is now believed that the compositions of ths invention are especially useful in the treatment of certain venerial diseases where it is sometimes difficult to ensure the return of the patient for further medication. The surprising prolonged blood levels obtained by using the compositions and methods of this invention are especially advantageous in such circumstances. A causitive pathogen susceptible to such treatment is *Neisseria gonorrhoeae*.

If desired the compositions of this invention may be used in medication in conjunction with amoxycillin trihydrate administered by the oral route, for example the oral amoxycillin trihydrate may be used during the day and the injectable compositions of this invention used to provide the desired overnight blood levels.

For use in animal therapy the unit and multi-dose forms will normally contain weights of amoxycillin trihydrate (measured as amoxycillin) of between 1.5 g and 12 g, for example about 2.5 g or about 10 g.

The compositions will be made up with the aqueous vehicle in conventional manner, and the concentration of the resultant suspension chosen so as to give a convenient injection volume for the domestic animal concerned. For example the injection volume will normally be in the range 0.5 to 25 ml. depending of course largely on the size of the animal concerned. The concentrations of the injected suspension will often be between 30 and 500 mg/ml., suitably 30-300 mg/ml.. Within this latter range concentrations such as 50, 100, 200 and 250 mg/ml. will often be particularly suitable due to ease of calculation of the required volume. It has been found that for a given dosage a higher concentration of injected suspension will often provide more prolonged effective blood levels of antibiotic than a lower concentration of injected suspension.

The actual weight of amoxycillin trihydrate administered in a single dose will depend in the usual way on various factors such as for example the nature of the bacterial infection, the severity of the infection and the domestic animal concerned. However we have found that a dose of between 3 and 20 mg/kg of amoxycillin trihydrate (measured as amoxycillin) and more suitably 7 mg/kg is generally suitable.

In a further aspect this invention provides a method of treating bacterial infections in domestic animals which method comprises the injection of a suspension of amoxycillin trihydrate which suspension was formed by the addition of an aqueous vehicle to a composition of this invention.

Once made up such suspensions have good stability.

An alternative view of this aspect of the invention provides a method of obtaining prolonged useful blood levels of amoxycillin in domestic animals which method comprises the parenteral administration of a suspension of amoxycillin trihydrate which suspension was formed by the addition of an aqueous vehicle to a composition of this invention.

The administration is normally intro-muscular or subcutaneous, but intravenous and intraperitoneal administration have also been safely and effectively used.

In veterinary practice it will be realised that repeated administration of an injectable formulation is often very inconvenient. The prolonged blood levels given by the composition of the invention in domestic animals such as sheep, pigs, cattle (particularly calves), horses, goats, dogs, cats and the like enables very good blood levels to be achieved in these animals with only two administrations per day, and good levels to be achieved with only one administration per day.

From the aforesaid it will be clear that a particularly suitable method of the invention will comprise the administration of one or two injections per day only, and a preferred method of the invention will often comprise the administration of not more than one injection per day.

It has further been found that when rather larger quantities of the composition are injected into animals, for example in the range 10 to 30 mg/kg of amoxycillin trihyrate (measured as amoxycillin) or even higher, suitably 15–25 mg/kg, blood levels effective against certain susceptible Gram-Positive bacteria may be maintained for as long as two days. Thus the invention further provides a method of treating susceptible Gran-Positive bacterial infections in domestic animals, which method comprises the injection not more than once every two days of an effective amount of amoxycillin trihydrate in the form of a composition of the invention suspended in an aqueous vehicle.

Normally the effective amount of amoxycillin trihydrate will be in the range 10 to 30 mg/kg measured as amoxycillin. Suitably this dosage is 15 to 25 mg/kg, for example about 20 mg/kg.

The following Examples illustrate the invention. A Pharmacological Section is also included to show the prolonged blood levels obtainable in humans and various domestic animals with the composition of the invention.

EXAMPLE 1

Compositions were prepared containing the following ingredients:

|  | A | B |  |
| --- | --- | --- | --- |
| Lecithin | 0.32 | 1.32 | % by wt. |
| Polyvinylpyrrolidone | 1.58 | 1.06 |  |
| Trisodium citrate | 3.16 | 2.64 |  |
| Sodium chloride | 0.63 | 0.00 |  |
| Methyl p-hydroxybenzoate | 0.28 | 0.47 |  |
| Propyl p-hydroxybenzoate | 0.03 | 0.05 |  |
| Amoxycillin trihydrate | 94.00 | 94.46 |  |

In the above compositions the amoxycillin trihydrate was present as fine particles substantially entirely coated by a mixture of the lecithin and polyvinylpyroolidone.

Composition A when reconstituted to give a suspension containing nominally 250 mg/ml. p.f.a. but with an overage of 10% (i.e. in fact containing 275 mg/ml p.f.a.) had the following stability at 20° C.

| Time | Chemical Assay | Bio Assay |
| --- | --- | --- |
| Initial | 273 mg/ml | 288 mg/ml |

| Time | Chemical Assay | Bio Assay |
| --- | --- | --- |
| 1 Month | 272 mg/ml | 284 mg/ml |
| 2 Months | 274 mg/ml | 288 mg/ml |
| 3 Months | 267 mm/ml | 278 mg/ml |

'P.f.a.' when used herein means 'measured as the free acid'.

EXAMPLE 2

Fine particles of amoxycillin trihydrate microencapsulated with a mixture of lecithin and polyvinylpyrollidone and having the proportions described for compositions A and B of Example 1 may be prepared by the methods of Belgian Patent No. 799,783 but adapting the processes therein to produce microcapsules of average diameter below 20μ. The polyvinylpyrrolidone used in such a process is normally of a parenteral grade such as Plasdone C-30, Plasdone C-15 or the like ('Plasdone' is a Trade Mark). The lecithin used in such a process is generally of a grade equivalent to Epikuron grade.

EXAMPLE 3

The compositions A and B of Example 1 were made by the following process:

A. NON-STERILE STAGE

1. Pass the amoxycillin trihydrate through a hammer mill (fast hammers forward) fitted with a 0.027" screen. Repeat with 0.006" screen.
2. Mill the sodium salts at 0.006", fast hammers forward.
3. Blend the amoxycillin and sodium salts in a planetary mixer for 30 minutes.
4. Dissolve the lecithin, polyvinylpyrollidone and esters in chloroform (approximately 30% by volume of the total batch weight).
5. Add the chloroform solution to the powders in the planetary mixer in 5 equal portions at 2–3 minute intervals.
6. Mix for a further 15 minutes.
7. Dry the powder in a Mitchell air oven in thin layers for 2½ hours at 40° C.
8. Remill the powder through a 0.006" screen.
9. Remix in a planetary mixer for 45 minutes.

B. STERILISATION STAGE EITHER Subject to
ethylene oxide gas for 12 hrs. a 125° F. using a 20/80 mixture of ethylene oxide/carbon dioxide at a pressure of 25 lbs/sq. ins., and then remill under aseptic conditions through an 0.006" screen.

OR Sterilise by irradiation with 2.5 Megarad dose.

C. FILLING

Fill the equivalent of 2.75 g amoxycillin free acid (2.5 g. nominal+10% overage) into sterile 50 mil. clear glass siliconised vials.

The weights of the constituents taken were as follows:

| | A | B |
| --- | --- | --- |
| Lecithin | 11 g. | 25 g. |
| Polyvinylpyrrolidone | 55 | 20 |
| Trisodium citrate | 110 | 50 |
| Sodium chloride | 22 | — |
| Methyl p-hydroxybenzoate | 9.9 | 9.0 |
| Propyl p-hydroxybenzoate | 1.1 | 1.0 |

| | A | B |
| --- | --- | --- |
| Amoxycillin trihydrate (at 84% p.f.a.) | 3270 | 1790 |

EXAMPLE 4

The following composition was prepared according to the process of Example 3, using the ethylene oxide sterilisation method:

| | Weight g. | Wt. of ingredient expressed as % of amoxycillin p.f.a. in the composition |
| --- | --- | --- |
| Lecithin | 78.4 | 0.4 |
| Polyvinylpyrrolidone | 392.1 | 2.0 |
| Trisodium citrate | 784.2 | 4.0 |
| Sodium chloride | 156.8 | 0.8 |
| Methyl p-hydroxybenzoate | 70.6 | 0.36 |
| Propyl p-hydroxybenzoate | 7.8 | 0.04 |
| Amoxycillin trihydrate (at 82.9% p.f.a.) | 23,649 | — |

PHARMACOLOGICAL SECTION

Test 1

Compositions A and B according to Example 3, and a composition C similar to A in which the amoxycillin trihydrate was replaced by ampicillin trihydrate, were made up to 15% wt/vol. suspensions by the addition of sterile water and administered by sub-cutaneous injection to Beagle dogs at a rate of 7 mg/kg bodyweight. Blood samples were taken at various time intervals and assayed for the presence of antibiotic. The results were as shown in the following Table in which the data for composition C is included for the sake of comparison:

| Time (hrs) | Approximate Blood Levels (μg/ml) | | |
| --- | --- | --- | --- |
| | A | B | C |
| ½ | 1.6 | 1.3 | 1.6 |
| 1 | 2.4 | 2.0 | 2.3 |
| 2 | 2.9 | 2.7 | 2.0 |
| 4 | 2.1 | 2.2 | 1.0 |
| 6 | 1.3 | 1.4 | 0.5 |
| 8 | 0.9 | 1.1 | 0.1 |

The prolonged blood levels obtained with compositions A and B particularly apparent at 4, 6 and 8 hours, when the levels obtained were approximately 2, 3 and 10 times respectively the levels obtained with composition C.

Compositions somewhat similar to composition C have been described in British Patent Specification Nos: 1,250,714, 1,289,693, and 1,316,625, and U.S. Pat. No: 3,733,404.

Test 2

Compositions A and C as used in Test 1 were compared in a cross-over study in 10 calves following intramuscular dosing at 7 mg/kg of amoxycillin trihydrate p.f.a. (suspension made up to 100 mg/ml of amoxycillin trihydrate p.f.a. in pyrogen free water). From 6 to 24 hours (the final time of sampling) after dosing the mean serum concentrations of amoxycillin given by A were significantly higher than those obtained with C.

| Time (hrs) | Blood Levels (μg/ml) | |
| --- | --- | --- |
| | A | C |
| 6 | 2.08 | 1.69 |
| 8 | 1.72 | 0.98 |
| 12 | 1.12 | 0.28 |
| 24 | 0.16 | 0.016 |

Test 3

The blood serum concentrations in calves with compositions A and C as used in Test 1 were compared after sub-cutaneous injection at 20 mg/kg of amoxycillin trihydrate p.f.a. (suspension made up to 250 mg/ml of amoxycillin trihydrate p.f.a. in water for injection).

After 48 hours it was found that composition A still gave levels of amoxycillin which would be effective against sensitive Gram-Positive organisms.

The results obtained are shown in the following Table:

| Time (hrs) | Blood Levels A | μg/ml C |
| --- | --- | --- |
| 1 | 3.34 | 2.95 |
| 2 | 3.65 | 3.68 |
| 4 | 3.45 | 3.73 |
| 6 | 3.29 | 3.74 |
| 8 | 2.97 | 3.32 |
| 24 | 0.72 | 0.54 |
| 30 | 0.31 | 0.08 |
| 48 | 0.03 | below .01 |

Test 4

The blood serum concentrations obtainable with composition A (as used in Test 1) in 6 fasted human volunteers was investigated. 270 mg. p.f.a. of the composition in 1.5 ml of sterile water was administered by intra-muscular injection to each volunteer. The injections were well tolerated. The mean blood levels of amoxycillin obtained at various times after dosing are shown below:

| Serum conc. μg/ml | | | | |
| --- | --- | --- | --- | --- |
| 1 hr | 2 hr | 3 hr | 4 hr | 6 hr |
| 1.62 | 1.97 | 2.25 | 1.62 | 0.95 |

This 6 hour figure is significantly higher than corresponding serum levels found at this time after similar tests in human volunteers with sodium amoxycillin.

Toxicity

No toxic effects have been observed in any of the tests carried out with the composition of the invention. It is believed that the injectable compositions of this invention have a similar low degree of toxicity as injectable sodium amoxycillin.

What we claimed is:

1. An antibacterial pharmaceutical composition providing prolonged effective antibiotic blood level, said composition comprising amoxycillin trihyrate in the form of fine particles of an average diameter of from $2\mu$ to $20\mu$ at least 95% of which have diameters of between $0.5\mu$ and $50\mu$ and which fine particles are coated with a dispersing agent consisting of polyvinylpyrrolidone and lecithin, the ratio of amoxycillin trihydrate to said dispersing agent being about 50:1, the ratio of polyvinylpyrrolidone to lecithin being about 5:1, said composition being in the form of a powder which may be constituted to a sterile, injectable suspension of amoxycillin trihydrate formed upon the addition of a pharmaceutically acceptable aqueous vehicle to a said composition and which suspension has enhanced stability and a pH in the range of 5.5.

2. A composition according to claim 1 wherein the fine particles have an average diameter of from $4\mu$ to $10\mu$ and at least 95% of the fine particles have diameters of between $1\mu$ and $30\mu$.

3. A composition according to claim 1 wherein the fine particles are 80 to 100% coated with the mixture.

4. A sterile, injectable composition comprising a composition according to claim 1 and a pharmaceutically acceptable aqueous vehicle, 5. A composition according to claim 4 wherein the pharmaceutically acceptable aqueous vehicle is water for injection.

6. A method for treating bacterial infections in humans and domestic mammals which method comprises injecting an antibacterially effective non-toxic amount of a composition according to claim 5 into a human or domestic mammal in need thereof thereby providing prolonged effective antibiotic blood level.

7. A method according to claim 6 wherein 10 to 30 mg/kg bodyweight of amoxycillin trihydrate, measured as amoxycillin, is injected.

* * * * *

UNITED STATES PATENT AND TRADEMARK OFFICE
CERTIFICATE OF CORRECTION

PATENT NO. : 4,876,086

DATED : October 24, 1989

INVENTOR(S) : John Sidney Dowrick

It is certified that error appears in the above-identified patent and that said Letters Patent is hereby corrected as shown below:

Title page, under heading [63] "Related U.S. Application Data", on line 4, change "Ser. No. 432,924" to -- Ser. No. 432,974--.

Signed and Sealed this

Fifteenth Day of January, 1991

Attest:

HARRY F. MANBECK, JR.

Attesting Officer

Commissioner of Patents and Trademarks